United States Patent [19]

Adkins et al.

[11] Patent Number: 5,312,971
[45] Date of Patent: May 17, 1994

[54] COLOR REDUCTION OF POLYMETHYLENE POLYPHENYL POLYISOCYANATES

[75] Inventors: Rick L. Adkins, New Martinsville, W. Va.; Clarence D. Blue, Dormagen, Fed. Rep. of Germany

[73] Assignee: Miles Inc., Pittsburgh, Pa.

[21] Appl. No.: 920,229

[22] Filed: Jul. 23, 1992

[51] Int. Cl.$^5$ .................. C07C 263/10; C07C 263/18
[52] U.S. Cl. ........................ 560/347; 560/25; 560/331; 560/333; 560/352
[58] Field of Search ............. 560/347, 352, 25

[56] References Cited

U.S. PATENT DOCUMENTS

| | | | |
|---|---|---|---|
| 2,733,254 | 1/1956 | Allen et al. | 560/347 |
| 3,277,139 | 10/1966 | Powers | 560/347 |
| 3,362,979 | 1/1968 | Bentley | 560/347 |
| 3,641,094 | 2/1972 | Arlt et al. | 560/347 |
| 3,912,600 | 10/1975 | Hatfield, Jr. et al. | 203/73 |
| 4,259,526 | 3/1981 | Dunlap et al. | 564/331 |
| 4,465,639 | 8/1984 | Hatfield, Jr. | 560/347 |
| 4,792,624 | 12/1988 | Hatfield, Jr. et al. | 564/333 |
| 5,207,942 | 5/1993 | Scherzer et al. | 252/182.2 |

*Primary Examiner*—José G. Dees
*Assistant Examiner*—Vera C. Clarke
*Attorney, Agent, or Firm*—Joseph C. Gil; N. Denise Brown

[57] ABSTRACT

The present invention is directed to a process for the production of polymethylene polyphenyl polyisocyanates by phosgenating the corresponding polyamines in solution in an inert organic solvent, removing excess phosgene, and stripping the solvent. The improvement resides in adding at least 0.02 parts by weight of reducing agent per 150 parts by weight of polyamine to the polyamines at any time prior to the stripping step.

4 Claims, No Drawings

COLOR REDUCTION OF POLYMETHYLENE POLYPHENYL POLYISOCYANATES

BACKGROUND OF THE INVENTION

Processes for the production of polymethylene polyphenyl polyamines and phosgenation of such polyamines to produce the corresponding polyisocyanates are well known in the art (see, e.g., U.S. Pat. Nos. 3,253,031, 3,260,751, 3,277,139, 3,277,173, 3,362,979, 3,496,229, 3,517,062, 3,641,094, 3,912,600 and 4,259,526).

In general, the process of producing the polyisocyanates includes the steps of phosgenating the polyamines in solution in an organic solvent, removing excess phosgene and then stripping the inert solvent. Some effort has been expended in reducing the color of the resultant polyisocyanates. U.S. Pat. No. 4,465,639 describes the addition of water prior to the solvent stripping step to reduce the color. U.S. Pat. No. 4,792,624 describes a specific polyamine recycling step during the aniline/formaldehyde reaction to cause a reduction in color of the corresponding polyisocyanate.

Czechoslovakian Patent 154,431 describes a method isolating isomers of diaminodiphenylmethane using a water extraction process. The reference describes the use of deoxidized water in the extraction and suggests that reducing agents should be added to the water in order to minimize staining of the isolated diamine.

DESCRIPTION OF THE INVENTION

The present invention is directed to the discovery that a relatively small amount of reducing agent added to the polyamines can result in a significant reduction in the color of the corresponding polyisocyanate. More particularly, the present invention is directed to a process for the production of polymethylene polyphenyl polyisocyanates comprising phosgenating the corresponding polyamines in solution in an inert organic solvent, removing excess phosgene, and stripping said solvent, the improvement wherein at least 0.02 parts by weight of reducing agent per 150 parts by weight of polyamine are added to said polyamines at any time prior to said stripping step.

As is well known in the art, the polymethylene polyphenyl polyamines are prepared by reacting aniline and formaldehyde in the presence of an aqueous acid catalyst (generally hydrochloric acid). The polyamines are isolated from the reaction mixture by first adding an excess of a neutralizing agent (generally sodium hydroxide), and then removing any excess neutralizing agent, water and aniline. The reducing agents of the present invention have been found to be effective in reducing the color of the corresponding polyisocyanate if they are added at any time following the addition of the neutralizing agent and before the stripping of the solvent used for phosgenation. Most effective results have been found where the addition of the reducing agent occurs just prior to phosgenation of the polyamine.

The details of the production of the polymethylene polyphenyl polyamines and the phosgenation to the corresponding polyisocyanates are known and described, for example, in U.S. Pat. Nos. 3,253,031, 3,260,751, 3,277,139, 3,277,173, 3,362,979, 3,496,229, 3,517,062, 3,641,094, 3,912,600, 4,259,526, 4,465,639 and 4,792,624, the disclosures of which are herein incorporated by reference.

Substantially any reducing agent can be used herein. Useful agents include boron hydrides, boron halides, metal hydrides, alkali metal alkoxides, and hindered phenols. Specific reducing agents include borane-tetrahydrofuran, sodium borohydride, dibromoborane-methyl sulfide, sodium cyanoborohydride, 9-borabicyclo[3.3.1]nonane, boron trifluoride etherate, lithium aluminum hydride, tributyltin hydride, diisobutylaluminum hydride, 2,6-di-tert-butyl-4-methylphenol, and sodium ethoxide. The presently preferred reducing agent is borane-tetrahydrofuran. The amount of reducing agent added can vary over a wide range. In general, at least 0.02 parts by weight of reducing agent per 150 parts by weight of the polyamine should be added. The upper limit is dictated by economics. In general, amounts in excess of 10 parts of reducing agent per 150 parts of polyamine do not show any increased advantage.

It may be necessary to quench the mixture when a highly reactive reducing agent (such as borane-tetrahydrofuran) is used. Substantially any relatively low molecular weight monohydroxyl compound can be used for this purpose. The main criteria is that the quenching material be strippable from the mixture. It is presently preferred to utilize low molecular weight monoalcohols, with methanol being most preferred. The amount of quenching agent used should be approximate to the amount of reducing agent added. The product resulting from the quenching can easily be removed (i.e., stripped) by application of a vacuum.

The color of polymethylene polyphenyl polyisocyanates can be broken down into two main absorptions in the UV-Visable spectrum—430 nm and 520 nm. A color decrease is herein defined as a decrease in either the 430 nm absorption or the 520 nm absorption.

The invention is further illustrated but is not intended to be limited by the following examples in which all parts and percentages are by weight unless otherwise specified.

EXAMPLES

EXAMPLE 1

150 parts of a commercially prepared polymethylene polyphenyl polyamine ("PMDA") were added to a 1-liter 3-necked flask equipped with a stirrer and reflux condenser under a nitrogen atmosphere. The product specifications for commercially produced PMDA used were as follows:

| | |
|---|---|
| Methylene bis(phenylamine) | 45–55% by weight |
| Polymethylene poly(phenylamine) | 45–55% by weight |
| Viscosity at 80° C. | 40–60 cps |
| Boiling point (77mm Hg) | 398° C. |
| Melting point range | 15–95° C. |

The PMDA was heated to 60° C. and 5.3 ml (0.0053 moles) of a 1M borane-tetrahydrofuran complex were added via a syringe. The temperature was increased to 100° C. and maintained at that temperature for one hour. The PMDA was cooled to 60° C. and 5 ml of methanol were slowly added to quench excess reducing agent. A vacuum was applied and the solution was heated to 150° C. to remove any low boiling components. The PMDA was cooled to 100° C. and poured into 1000 parts of monochlorobenzene.

2000 parts of monochlorobenzene were cooled to 5° C. and charged with 6 moles of phosgene. The PMDA/monochlorobenzene solution was then added to the phosgene/monochlorobenzene solution. The reacting solution was slowly heated to 130° C. and held at 130° C. for one hour while maintaining a 1 mole/hour phosgene purge. Phosgene was then removed by purging with nitrogen at 130° C. for 30 minutes. The solvent was then vacuum distilled to produce the final polymethylene polyphenyl polyisocyanate ("PMDI").

When compared to a polymethylene polyphenyl polyisocyanate produced in exactly the same manner but without addition of the reducing agent, the PMDI showed a 75% decrease in color in the 430 nm absorption and a 86% decrease in color in the 520 nm absorption.

The example was repeated except that there was no methanol quench. When compared to a polymethylene polyphenyl polyisocyanate produced in exactly the same manner but without addition of the reducing agent, the resultant PMDI showed a 79% decrease in color in the 430 nm absorption and a 91% decrease in color in the 520 nm absorption.

EXAMPLE 2

1000 parts of monochlorobenzene were added to a 2-liter 3-necked flask equipped with a stirrer and reflux condenser under a nitrogen atmosphere. The monochlorobenzene was heated to 60° C. and 149 parts of the same PMDA used in Example 1 were added. 16.0 ml (0.016 moles) of a 1M borane-tetrahydrofuran complex was added and the mixture was heated at 100° C. for 30 minutes. The reaction solution was then cooled to 50° C. and 1.54 parts of methanol were added.

2000 parts of monochlorobenzene were cooled to 5° C. and charged with 6 moles of phosgene. The PMDA/monochlorobenzene solution was then added to the phosgene/monochlorobenzene solution. The reacting solution was slowly heated to 130° C. and held at 130° C. for one hour while maintaining a 1 mole/hour phosgene purge. Phosgene was then removed by purging with nitrogen at 130° C. for 30 minutes. The solvent was then vacuum distilled to produce the final polymethylene polyphenyl polyisocyanate ("PMDI").

When compared to a polymethylene polyphenyl polyisocyanate produced in exactly the same manner but without addition of the reducing agent, the PMDI showed a 80% decrease in color in the 430 nm absorption and a 90% decrease in color in the 520 nm absorption.

The example was repeated except that there was no methanol quench. When compared to a polymethylene polyphenyl polyisocyanate produced in exactly the same manner but without addition of the reducing agent, the resultant PMDI showed a 86% decrease in color in the 430 nm absorption and a 92% decrease in color in the 520 nm absorption.

EXAMPLE 3

150 parts of the same PMDA used in Example 1 were dissolved in 1000 parts of monochlorobenzene. 2000 parts of monochlorobenzene were cooled to 5° C. and charged with 6 moles of phosgene. The PMDA/monochlorobenzene solution was then added to the phosgene/monochlorobenzene solution. The reacting solution was slowly heated. Once the temperature reached 90° C., 16.0 ml of the borane-tetrahydrofuran complex used in Example 1 were added. Heating was continued until the temperature reached 130° C. The mixture was held at 130° C. for one hour while maintaining a 1 mole/hour phosgene purge. Phosgene was then removed by purging with nitrogen at 130° C. for 30 minutes. The solvent was then vacuum distilled to produce the final polymethylene polyphenyl polyisocyanate ("PMDI").

When compared to a polymethylene polyphenyl polyisocyanate produced in exactly the same manner but without addition of the reducing agent, the PMDI showed a 62% decrease in color in the 430 nm absorption and a 83% decrease in color in the 520 nm absorption.

EXAMPLE 4

150 parts of the same PMDA used in Example 1 were dissolved in 1000 parts of monochlorobenzene. 2000 parts of monochlorobenzene were cooled to 5° C. and charged with 6 moles of phosgene. The PMDA/monochlorobenzene solution was then added to the phosgene/monochlorobenzene solution. The reacting solution was slowly heated to 130° C. and held at that temperature for while maintaining a 1 mole/hour phosgene purge. The reaction solution was cooled to 60° C. while continuing the phosgene purge. 16.0 ml of the borane-tetrahydrofuran complex used in Example 1 were added and the reaction solution was stirred at 60° C. for 20 minutes under phosgene. After 20 minutes, the solution was heated to 130° C. under nitrogen to remove the phosgene. The solvent was then vacuum distilled to produce the final polymethylene polyphenyl polyisocyanate ("PMDI").

When compared to a polymethylene polyphenyl polyisocyanate produced in exactly the same manner but without addition of the reducing agent, the PMDI showed a 13% decrease in color in the 430 nm absorption and a 68% decrease in color in the 520 nm absorption.

EXAMPLE 5

150 parts of the PMDA used in Example 1 were dissolved in 1000 parts of monochlorobenzene. 2000 parts of monochlorobenzene were cooled to 5° C. and charged with 6 moles of phosgene. The PMDA/monochlorobenzene solution was then added to the phosgene/monochlorobenzene solution. The reacting solution was slowly heated to 130° C. and held at 130° C. for one hour while maintaining a 1 mole/hour phosgene purge. Phosgene was then removed by purging with nitrogen at 130° C. for 30 minutes. The solution was then cooled to 60° C. and 16.0 ml of the borane-tetrahydrofuran complex used in Example 1 were added. The mixture was stirred for 30 minutes at 60° C. The solvent was then vacuum distilled to produce the final polymethylene polyphenyl polyisocyanate ("PMDI").

When compared to a polymethylene polyphenyl polyisocyanate produced in exactly the same manner but without addition of the reducing agent, the PMDI showed a 35% decrease in color in the 430 nm absorption and a 73% decrease in color in the 520 nm absorption.

EXAMPLE 6

150 parts of a commercial available polymethylene polyphenyl polyisocyanate (MONDUR MR, available from Miles Inc., having an NCO content of about 32% by weight and a viscosity of form 150 to 250 cps at 25° C.) were added to a 1 liter, 3-necked flask equipped with a stirrer and condenser under a nitrogen atmosphere. 16.0 ml of the borane-tetrahydrofuran complex used in Example 1 were added to the PMDI and the mixture was stirred for 1.5 hours at 25° C. A vacuum was applied and the isocyanate heated to 70° C. to remove residual tetrahydrofuran. The treated PMDI showed a 21% decrease in color in the 430 nm absorption and a 27% increase in color in the 520 nm absorption.

EXAMPLE 7

This example simulated the product mixture exiting a commercial facility immediately after neutralization of the acidic polymethylene polyphenyl polyamine. To a 1-liter, 3-necked flask equipped with stirrer and condenser were added 150 parts of the PMDA used in Example 1, 38 parts of aniline, 14 parts of a 50% sodium hydroxide solution, and 219 parts of water. The mixture was stirred until homogeneous. 1 part of sodium borohydride was then added. The mixture was heated at 100° C. for 2 hours. The amine and water phases were separated and the amine layer was washed with two 300 ml portions of water. Residual water and aniline were removed by heating to 160° C. under a vacuum.

150 parts of the amine were dissolved in 1000 parts of monochlorobenzene. 2000 parts of monochlorobenzene were cooled to 5° C. and charged with 6 moles of phosgene. The amine/monochlorobenzene solution was then added to the phosgene/monochlorobenzene solution. The reacting solution was slowly heated to 130° C. and held at 130° C. for one hour while maintaining a 1 mole/hour phosgene purge. Phosgene was then removed by purging with nitrogen at 130° C. for 30 minutes. The solvent was then vacuum distilled to produce the final polymethylene polyphenyl polyisocyanate.

When compared to an isocyanate produced in exactly the same way but without the addition of the reducing agent, the PMDI showed a 47% reduction in the 430 nm absorption and a 39% reduction in the 520 nm absorption.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the production of polymethylene polyphenyl polyisocyanates comprising phosgenating the corresponding polyamines in solution in an inert organic solvent, removing excess phosgene, and stripping said solvent, the improvement wherein at least 0.02 parts by weight of reducing agent per 150 parts by weight of polyamine are added to said polyamines at any time prior to said stripping step.

2. The process of claim 1, wherein said reducing agent is selected from the group consisting of boron hydrides, boron halides, metal hydrides, alkali metal alkoxides and hindered phenols.

3. The process of claim 1, wherein said reducing agent is selected from the group consisting of borane-tetrahydrofuran, sodium borohydride, dibromoborane-methyl sulfide, sodium cyanoborohydride, 9-borabicyclo[3.3.1]nonane, boron trifluoride etherate, lithium aluminum hydride, tributyltin hydride, diisobutylaluminum hydride, 2,6-di-tert-butyl-4-methylphenol, and sodium ethoxide.

4. The process of claim 3, wherein said reducing agent is borane-tetrahydrofuran.

* * * * *